(12) United States Patent
Iqbal et al.

(10) Patent No.: US 11,717,148 B2
(45) Date of Patent: Aug. 8, 2023

(54) PROCTOSCOPE AND METHODS OF USE

(71) Applicant: SURGEASE INNOVATIONS LIMITED, Lancashire (GB)

(72) Inventors: Fareed Iqbal, Maidenhead (GB); Amina Mahmood, London (GB); Choukri Mecheraoui, London (GB)

(73) Assignee: SURGEASE INNOVATIONS LIMITED, Lancashire (GB)

( * ) Notice: Subject to any disclaimer, the term of this patent is extended or adjusted under 35 U.S.C. 154(b) by 0 days.

(21) Appl. No.: 17/824,724

(22) Filed: May 25, 2022

(65) Prior Publication Data
US 2022/0354358 A1    Nov. 10, 2022

Related U.S. Application Data

(63) Continuation of application No. PCT/GB2021/051450, filed on Jun. 10, 2021.

(30) Foreign Application Priority Data

Jun. 10, 2020   (GB) .................................... 2008829

(51) Int. Cl.
*A61B 1/31*    (2006.01)
*A61B 1/00*    (2006.01)
*A61B 1/05*    (2006.01)

(52) U.S. Cl.
CPC ............ *A61B 1/31* (2013.01); *A61B 1/00177* (2013.01); *A61B 1/00181* (2013.01); *A61B 1/05* (2013.01)

(58) Field of Classification Search
CPC ... A61B 1/31; A61B 1/00181; A61B 1/00177; A61B 1/00174; A61B 1/05;
(Continued)

(56) References Cited

U.S. PATENT DOCUMENTS

2005/0014994 A1*  1/2005  Fowler .................. A61B 34/32
                                                              600/102
2007/0177008 A1   8/2007  Bayer et al.
(Continued)

FOREIGN PATENT DOCUMENTS

JP        3628915 B2       3/2005
WO     2007087421 A2       8/2007

OTHER PUBLICATIONS

International Search Report and Written Opinion in PCT International Application No. PCT/GB2021/051450 dated Sep. 7, 2021.
(Continued)

*Primary Examiner* — Ryan N Henderson
*Assistant Examiner* — Pamela F Wu
(74) *Attorney, Agent, or Firm* — Greenberg Traurig, LLP; David J. Dykeman; Roman Fayerberg

(57) ABSTRACT

Provided is a scope that can comprise a tubular casing, a proximal end, a distal end, an internal volume, a longitudinal axis of extension extending from the distal end to the proximal end, a vertical axis extending perpendicularly to the longitudinal axis of extension and one or more apertures along a length L of the longitudinal axis of extension; a handle having a proximal end and a distal end; and image capture devices each located within the internal volume of the tubular casing.

20 Claims, 16 Drawing Sheets

(58) Field of Classification Search
CPC ............ A61B 1/00163; A61B 1/00179; A61B 1/00183; A61B 1/04; A61B 1/0017; A61B 1/0676
USPC ........ 600/109, 128, 170, 175, 164, 160, 129
See application file for complete search history.

(56) References Cited

U.S. PATENT DOCUMENTS

| | | |
|---|---|---|
| 2007/0185384 A1* | 8/2007 | Bayer ..................... A61B 1/31 600/129 |
| 2007/0293720 A1 | 12/2007 | Bayer |
| 2008/0021274 A1 | 1/2008 | Bayer et al. |
| 2009/0231419 A1* | 9/2009 | Bayer ................ A61B 1/00179 348/76 |
| 2009/0259110 A1 | 10/2009 | Bastia et al. |
| 2011/0160530 A1 | 6/2011 | Ratnakar |
| 2013/0116506 A1 | 5/2013 | Bayer et al. |
| 2017/0319233 A1* | 11/2017 | Fonger ............... A61B 17/3478 |

OTHER PUBLICATIONS

International Preliminary Report on Patentability in PCT International Application No. PCT/GB2021/051450 dated Feb. 2, 2022.

* cited by examiner

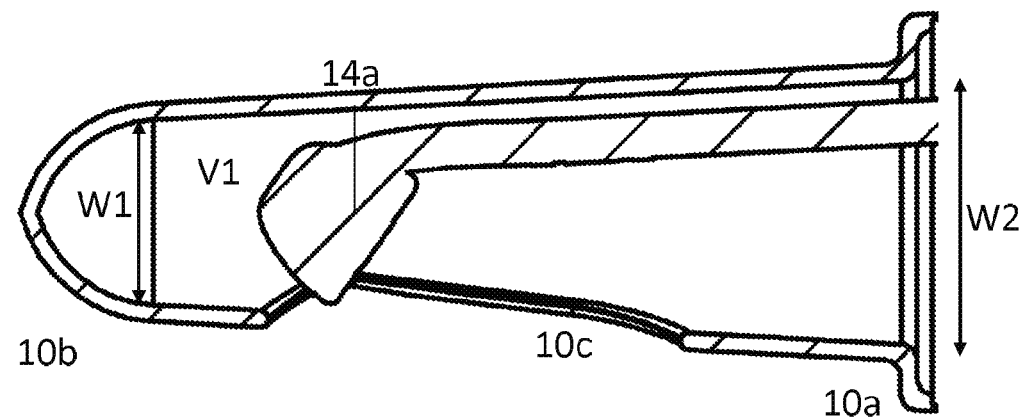
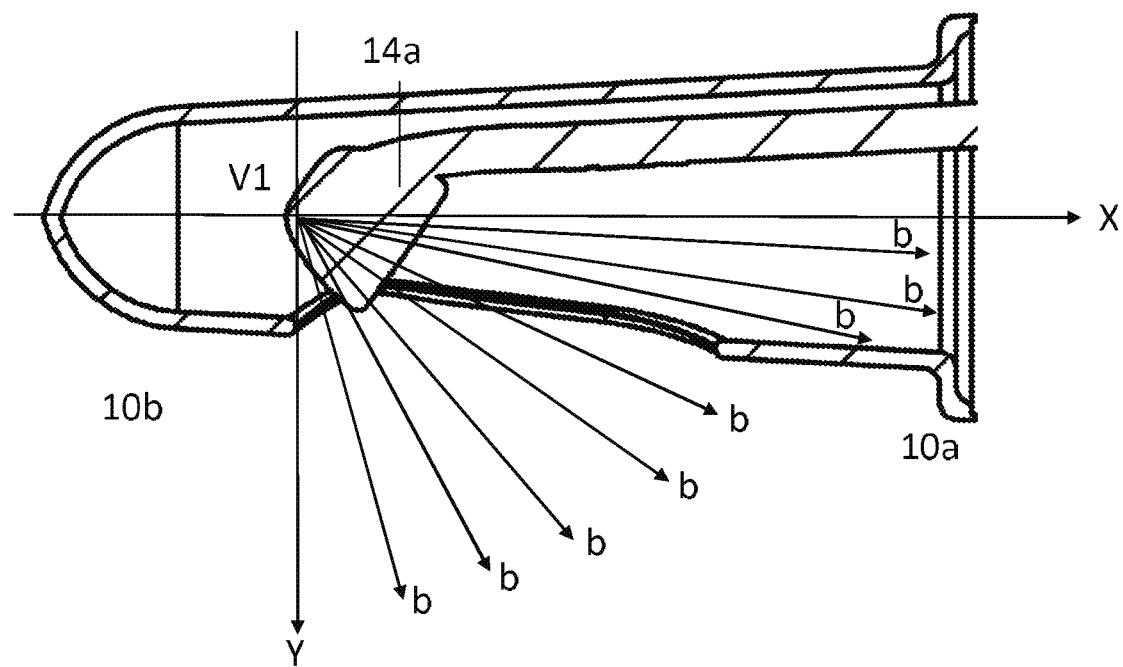
Figure 5

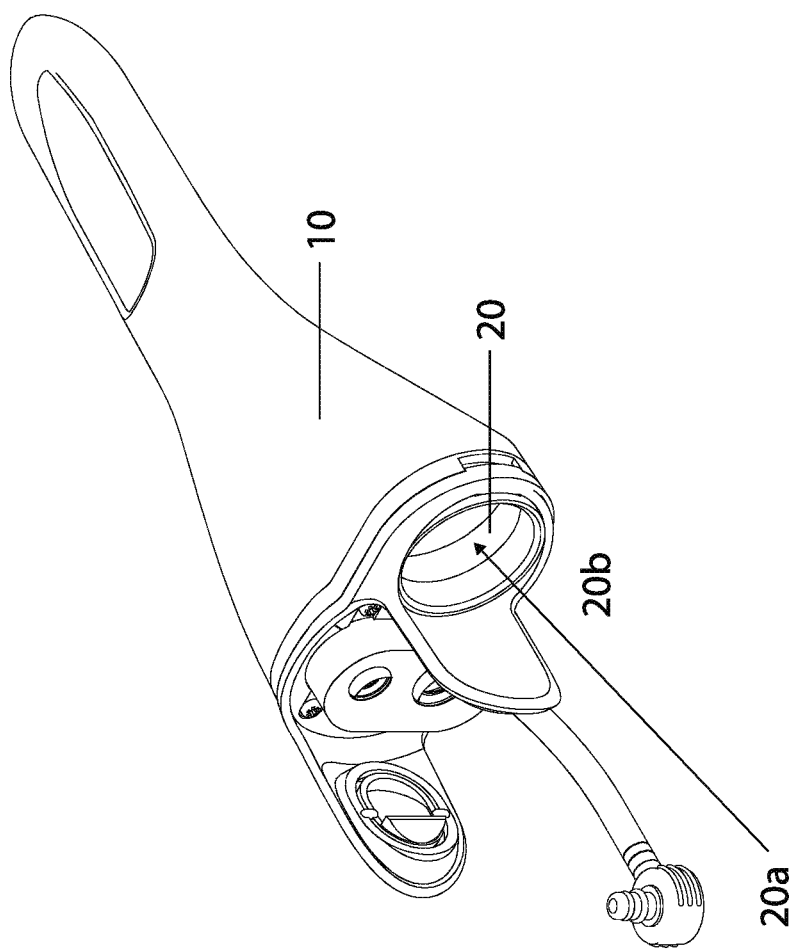

PROCTOSCOPE AND METHODS OF USE

RELATED APPLICATION

This application is a U.S. bypass continuation patent application of PCT International Patent Application No. PCT/GB2021/051450, filed Jun. 10, 2021, which claims priority to and the benefit of GB Application No. 2008829.0, filed Jun. 10, 2020, the contents of each of which are incorporated herein by reference in their entireties.

FIELD

The present disclosure provides an improved scope for use in medical investigations and surgical procedures. In particular, the scope is for insertion into the anus and can be used by a physician to investigate the internal structures of the anus and rectum and furthermore, can be used by the physician to perform surgical procedures.

BACKGROUND

The anal canal is the terminal segment of the gastrointestinal tract. It extends 2 cm from the dentate line to the anal verge (the outermost tissue seen externally) and usually measures 3.5 cm to 4 cm in length. Men usually have longer anal canals compared to women. The anus forms part of the anal canal complex which also includes the external and internal sphincters and the distal rectum. Its principle function is to provide continence and relay feedback to the higher brain centres when rectal emptying is desired. The anal canal complex is a co-ordinated system providing reflex information to auto-govern its end function. The recto-anal inhibitory reflex, is a good example of this structure; sudden increases in rectal pressure, results in reflex relaxation of the internal sphincters so rectal emptying can occur, but this can be inhibited by the external sphincters which remain under voluntary control; this allows people to confirm that they are in a socially suitable place to allow rectal emptying.

Disorders of the anal canal complex results in incontinence, pain, bleeding, itching, constipation and incomplete bowel emptying. The anus and the sphincters provide sufficient resistance to high rectal pressures so continence is maintained. It is unsurprising, therefore, that chronically abnormal pressures result in diseases of the anal canal which include haemorrhoids, fissue-in-ano, fistula-in-ano, infection, pruritis and haematomas. Though additional factors contribute to the progression of each disease, including systemic diseases, poor toileting behaviours and diets void of fibre have significant influence on disease pathogenesis.

Anal canal appearance and dysfunction can be surrogate markers of general rectal and/or gastrointestinal tract health. By means of example, a fissure-in-ano- defined as a linear tear in the anal canal, is commonly seen in inflammatory bowel diseases like Ulcerative colitis and should be excluded when observed in patients. Peri-anal infection and abscesses can result from Crohn's disease and rectal Tuberculosis whilst haemorrhoids can occur secondary to rectal growths like cancer. It is of upmost importance to inspect the rectum when diagnosing anal disease.

Anal cancer, though rare, occurs in approximately 1% of all colorectal cancer cases. Approximately 1500 cases are diagnosed each year in the UK and 8000 cases in the US, with incidence rising sharply since the 1990's. Risk factors include smoking, older age, immune deficiency, HPV exposure, certain sexual behaviours which includes multiple partners. It is important to assess the extent of anal cancer spread as some growths extend into the rectum and conversely rectal cancer can extend into the anus which can be mistaken for an anal cancer primary. Making this distinction on examination is important as it dictates treatment strategy.

Benign diseases affecting the anus are extremely common and account for thousands of emergency and outpatient consultations each year. In the US, approximately 4.4% of the adult population report haemorrhoidal symptoms and millions are spent on treating these disorders each year.

Anoscopy (sometimes referred to as proctoscopy) is the examination of the anus, anal canal and distal rectum with a proctoscope. It involves insertion of a hollow sheath into the anus which acts to part the tissues sufficiently so that the target anatomy can be directly visualised within the lumen of the sheath. Special preparation for proctoscopy is not usually required, but an enema can be administered if appropriate. For the examination, patients are placed in a relaxed position, such as the left lateral or lithotomy positions. The proctoscope is carefully introduced into the anus; different sizes of instrument can be used depending on the anatomic conditions. The proctoscope has an internal obturator that provides internal illumination when the light source is withdrawn, and with its conical tip it makes it easier to introduce the proctoscope. The instrument has adequate lubricant applied for introduction and is inserted in alignment with the perineal region in the direction of the navel, with rotation. It is useful to ask the patient to bear down in order to relax the sphincters. A digital rectal examination also aids the process of introduction, as it already leads to slight dilation and anesthetisation of the anal canal. After the sphincter region has been passed (3-5 cm from the anus), the proctoscope/anoscope is tilted sacrally to follow the anatomic course of the rectum (the anorectal flexure). The proctoscope should be warmed to a lukewarm temperature, and intubation should not be carried out blindly against resistance. The proctoscope should be introduced as far as the stop ring to ensure complete assessment of the anal canal, even in the presence of a funnel anus. The proctoscope is slowly withdrawn with rotatory movements that allow visualization of the entire circumference. Due to its length, the proctoscope is much easier to guide than the rectoscope. Due to the shortness of the instrument, the light yield is also superior to a rectoscope. Despite this, it is difficult to expose discrete findings, so that locations that were conspicuous during the digital examination need to be assessed with particular care. In addition, it is advisable to separately assess sites of predilection for proctologic diseases (crypt regions, haemorrhoid complexes at the 3-o'clock, 7-o'clock, and 11-o'clock positions, fissures at the 6-o'clock position, etc.).

Proctoscopy is performed alongside rigid rectoscopy; the latter refers to a similar instrument but is much longer (20-25 cm) and visualises the rectum and distal colon with a closed gas-tight seal. The two methods have specific indications and should not be considered complimentary to each other. The utility of rigid rectoscopy has declined in recent years with colonoscopy being favoured due largely to poor views and little diagnostic value. It only continues to be of value in specific indications such as measuring the distance between rectal tumours and the anal verge, as well as identifying rectoceles and intussusceptions. By contrast, proctoscopy has unique benefits over rectoscopy and is superior for assessing diseases in the anal canal. Flexible endoscopes are far superior to rigid rectoscopes but in the case of proctoscopes even colonoscopy cannot achieve the views possible with the former. The proctoscope physically holds the anal canal open without insufflation which makes hemorrhoidal disease assessment particular easy, however the lack of insufflation makes assessment of the anorectal junction (the point at which the anal complex and rectum join) difficult. This region can harbour malignancies and without appropriate insufflation, occult lesions can hide behind rectal folds and in the anorectal sulci. One disadvantage with both proctoscopy and rectoscopy is that is fails to provide an adequate view of the anorectal junction. This view is usually achieved with the J-manoeuvre during colonoscopy which gives an unobstructed view of this region. Additionally, it is very difficult to document and demonstrate the findings from rigid rectoscopy and proctoscopy, as the conventional techniques do not include a video connection.

A historically high rate of surgical failure in anal disease management and the need for repeat surgery were common experiences of doctors dealing with these conditions. The advent of improved proctoscopy instrumentation has allowed a higher percentage of disease healing, improved anatomical and functional integrity assessment of the anal canal and a greater acceptance by patients to undergo these procedures. The turning point has included a better comprehension of the anatomy. However this level of detail can currently only be determined by magnetic resonance imaging and endoanal-endorectal ultrasound. The latter is becoming the paramount diagnostic instrument of use by colorectal surgeons, as it allows a clear understanding of underlying anatomic defects. Through the use of new diagnostic technologies (2D-3D endoanal ultrasonography and pelvic-perineal MRI) and morpho-functional diagnostic methods (anorectal manomentry, defecography, anal electromyography, and evaluation of motor latency time of the pudendal nerve), a better anatomical and physiological definition is possible which allows better definition of the clinic characteristics and hence appropriate therapy selection.

Unfortunately, the aforementioned investigations like MRI and endo-anal US are not available at point of care, they are expensive, and are contra-indicated in patients with internal metallic objects (MRI) and in the case of endo-anal US, very user-dependent. Clinicians cannot currently make accurate assessments of the whole anal complex with the current state of bedside instruments. Anatomically, the anal complex is made up of multiple vectors and planes and acquiring these views is not possible with proctoscopy. Variables that contribute to this include:

Anatomy: the anus is naturally closed tight which requires the examiner to part the anus with force to visualise the internal mucosa. The anal complex has multiple planes and vectors and is partly situated internally. The anal canal can harbour disease at any circumferential location so a 360degree assessment must be carried out. This brings ergonomic challenges and patient discomfort when the scope is twisted and rotated during the procedure Patient position: The position of choice during examination depends on the equipment available, the examiner's preference and experience, and the patient's habitus. The three most frequent positions for proctologic examinations are lithotomy, prone knee-elbow position, and left lateral. The lithotomy position allows for direct doctor-patient communication, eye contact and patient comfort but requires specialist bed stirrups; prone knee-elbow position facilitates the inspection of the perianal region with good buttock retraction but it is relatively uncomfortable and embarrassing for the patient; the left lateral position is comfortable and readily practicable but with larger patients, the buttocks need to be parted away to visualise the anus.

Limitations of current instruments: Limitations of proctoscopes include, poor lighting when deeper structures require visualisation. When the insertion obturator is removed, the open hollow sheath allows faeces to pass inside the channel with obscures the view and make the procedure very unhygienic for the user. In some series, up to a third of doctors have been found to harbour faecal flora on their face after examination. The handle of the proctoscope is situated close to the insertion member, which in patients with larger buttocks, means the operating hand has to be pressed closed to the patients perineum. This is uncomfortable for both the user and the patient.

Examiner positioning: The doctor must peer directly down the sheath to identify pathology. This makes the procedure unpleasant from the direct exposure of odour and flatus.

Interventional limitations: Identified pathologies can be treated during proctoscopy which includes rubber band ligation of haemorrhoids. Almost all anal therapies are conducted with poor views, as the inherent nature of the instruments mean that when the operating hand is used to deliver the therapy, the views are obscured by the therapy administering hand. Additionally, it is extremely important for treatment to be delivered above an anatomical line called the dentate line. This demarcates the junction between the embryonic hindgut and ectoderm, which are innervated by visceral and somatic nerves respectively. This means there is no sensation felt above the dentate line but below it, the sensation is heightened. If inadvertent therapy below the dentate line is administered, it is extremely painful and can lead to patient collapse. Current proctoscopes cannot provide a suitable view of the dentate line during treatment delivery. The ideal view of the dentate line is seen during the J-manoeuvre, which as mentioned previously, is not possible with any rigid endoscope. Visualising the dentate line from above during an anal intervention would invite huge advantages particularly if it can be done with ideal patient and user positioning and comfort.

There is a clear need to provide an improved scope, in particular an improved anoscope, to address the current limitations with conventional scope devices.

SUMMARY

In one aspect, a scope for insertion into the anus is provided, wherein said scope comprises:
(a) a tubular casing (10), a proximal end (10a), a distal end (10b), an internal volume (V1), a longitudinal axis of extension (X) extending from the proximal end (10a) to the distal end (10b), a vertical axis (Y) extending perpendicularly to the axis of extension (X) and one or more openings (10c) along the length L of the longitudinal axis of extension (X); a handle (12) having a proximal end (12a) and a distal end (12b); and one or more image capture devices (14) located towards the distal end (10b) of the tubular casing (10) and within the internal volume (V1) of the tubular casing (10),
wherein the one or more image capture devices (14) is a rearward camera (14a) looking along an axis (b) extending between the longitudinal axis of extension (X) and the vertical axis (Y).

In some embodiments, the scope comprises an intermediate portion (16) having a proximal end (16a) and a distal end (16b) and wherein the distal end (16b) of the intermediate portion (16) is connected to the proximal end (10a) of the tubular casing (10) and the proximal end (16a) of the intermediate portion (16) is connected to the handle (12).

In some embodiments, the scope further comprises a sideward camera (14b) located within the internal volume (V1) of the tubular casing (10) and wherein the sideward camera is looking along the vertical axis (y) and through the opening (10c) in the tubular casing (10).

In some embodiments, the scope further comprises a forward camera (14c) looking along the longitudinal axis of extension (X) from the proximal end (10a) to the distal end (10b) of the tubular casing (10). The forward camera (14c) is located within the internal volume of the tubular casing (10) providing a viewpoint, along the longitudinal axis of extension (X) from the proximal end (10a) to the distal end (10b), through the internal space of the tubular casing (10).

In some embodiments, the scope, further comprises:
a) a sideward camera (14b) located within the internal volume (V1) of the tubular casing (10) and wherein the sideward camera is looking along the vertical axis (Y) and through the opening (10c) in the tubular casing (10); and
b) a forward camera (14c) looking along the longitudinal axis of extension (X) from the proximal end (10a) to the distal end (10b) of the tubular casing (10).

In some embodiments, the scope further comprises an projection (18) having a first end (18a) mounted on the distal end of the intermediate portion (16b) and extending along axis (X) towards a distal (10b) end within the tubular casing (10) and wherein rearward camera (14a) is mounted on the projection (18). In some embodiments, the projection is bifurcated. In some embodiments, the sideward camera (14b) is additionally mounted on the projection (18).

In some embodiments, the scope further comprises a projection (18) having a first end (18a) mounted on the distal end of the intermediate portion (16b) and extending along axis (X) towards a distal (10b) end within the tubular casing (10) and wherein the sideward camera (14b) is mounted on the projection (18). In some embodiments, the projection is bifurcated.

In some embodiments, as shown in FIG. 15, the scope comprises two projections (27, 28), each projection having a first end mounted on the distal end of the intermediate portion (16b) and extending along axis (X) towards a distal (10b) end within the tubular casing (10) and wherein the rearward camera (14a) and optionally the sideward camera (14b) is mounted on the first projection (27) and wherein the forward camera (14c) is mounted on the second projection (28). The projections can alternatively be mounted on the distal end of the intermediate portion via a connecting assembly (29). In some embodiments, the projections are extendable and can project forward and backward along axis (X).

In some embodiments, the intermediate portion (16) is further comprised of an outer surface, an inner surface and a support member (24) attached to the inner surface and wherein the forward camera (14c) is mounted on the support member. The support member is located within the internal volume of the tubular casing (10). In some embodiments, the tubular casing (10) is rigid.

In some embodiments, the intermediate portion (16a) further comprises a conduit (20) having a first external end (20a) and a second internal end (20b) and extending from outside of said scope into the interior of the tubular casing (10) for insertion of surgical instruments into the internal volume (v2). In some embodiments, the first external end (20a) is within the intermediate portion (16). In some embodiments, the intermediate portion (16) further comprises a cover (22) for covering the first external end (20a) of the conduit (20). In some embodiments, the scope further comprises a latch (35) for releasably securing the cover (22) to the intermediate portion (16). In some embodiments, the scope further comprises a latch release for releasing the latch and being positioned on the handle (12).

In some embodiments, the scope further comprises a pressurising mechanism (28) for pressurising the interior of the tubular casing (10). In some embodiments, the pressurising mechanism (28) is contained within the handle (12) and comprises a bellows (30).

In some embodiments, the cross-sectional profile of the tubular casing (10) has a maximum diameter (D2) at the proximal end (10a) of the tubular casing (10) and tapers to a minimum diameter (D1) at the distal end (10b) of the tubular body. In some embodiments, the scope further comprises one or more covers for the one or more openings (1c) in the tubular casing (10). In some embodiments, the tubular casing (10) is removably connected to the intermediate portion (16a).

In some embodiments, the scope further comprises a light source for projection light into the interior of the casing (10). In some embodiments, the intermediate portion (16) is rotatably mounted on the handle (12) for rotation about said longitudinal axis (X).

In one aspect, a tubular casing (10) having a longitudinal axis of extension (X), a proximal end (10a), a distal end (10b), an internal volume (V1) and one or more openings (10c) along the length L of the longitudinal axis of extension (X) for a scope as defined herein is provided.

In one aspect, a scope for insertion into the anus is provided, wherein said scope comprises:
(a) a handle (12) having a proximal end (12a) and a distal end (12b) and a longitudinal axis of extension (X) extending from the proximal end (12a) to the distal end (12b); and
(b) a projection (18) having a first end (18a) mounted on the distal end of the handle (12b) and projecting in the opposite direction to the proximal end of the handle (12a) and wherein a rearward camera is mounted on the projection and wherein the rearward camera looks along the longitudinal axis of extension (x) towards the proximal end of the handle (12a).

In further aspect the present disclosure relates to a scope for use in the sampling of the anus. In further aspect the present disclosure relates to a scope for use in the sampling of the rectum.

In further aspect the present disclosure relates to a method of treatment comprising inserting a scope into the anus and sampling, performing biopsy, removing, cauterizing or otherwise treating the anal canal.

In further aspect the present disclosure relates to a method of anorectal diagnosis comprising inserting the rigid scope into the anus, viewing, performing biopsy or otherwise examining the anus, and comparing the results with images or biopsies of known normal anus to diagnose disease.

In further aspect the present disclosure relates to a method of determining the presence or absence of anorectal disease, comprising inserting the rigid scope into the anus, viewing, performing biopsy or otherwise examining the anus, and comparing the results with images or biopsies of known normal anus to thereby determine if the patient's anus is diseased or is at risk of developing disesase, and optionally requires a suitable treatment.

In a further aspect, there is provided a method of diagnosis and treatment, optionally to the anorectal region, comprising
a) inserting a scope as described herein into the anus, viewing, performing biopsy or otherwise examining the anus, and comparing the results with images or biopsies of known normal anus to diagnose disease; and b) treating the anus according to the disease diagnosis in a).

DESCRIPTION OF FIGURES

The present disclosure will now be described with reference to the accompanying diagrammatic drawings in which:

FIG. 5 is a cross-sectional view of the tubular casing (10) and shows one example of a rearward camera (14*a*) positioned within the internal volume (V1) of the tubular casing. Several examples of axis (b) are displayed in the second cross-sectional view.

FIG. 16 provides a perspective view of the tubular casing and the conduit.

DETAILED DESCRIPTION

WO 2007/087421 describes a flexible endoscope for use in colonoscopy/sigmoidoscopy. This is a traditional type of endoscope that uses cameras on the external surface of the flexible tube of the device to view the internal surface or tissue of the body. Notably, these type of endoscopes do not comprise one or more openings, in particular one or more apertures, in the tubular casing of the device. Such endoscopes cannot therefore permit viewing of the body surface or tissue within the internal volume of the tube of the device.

In one aspect, an improved scope is provided. In a preferred embodiment, the scope is an anoscope used primarily for the investigation of the anus. However, the scope may also be other types of scope, for an example an endoscope, a proctoscope or a rectoscope. The present disclosure will now be described with reference to the figures.

Figure 1:
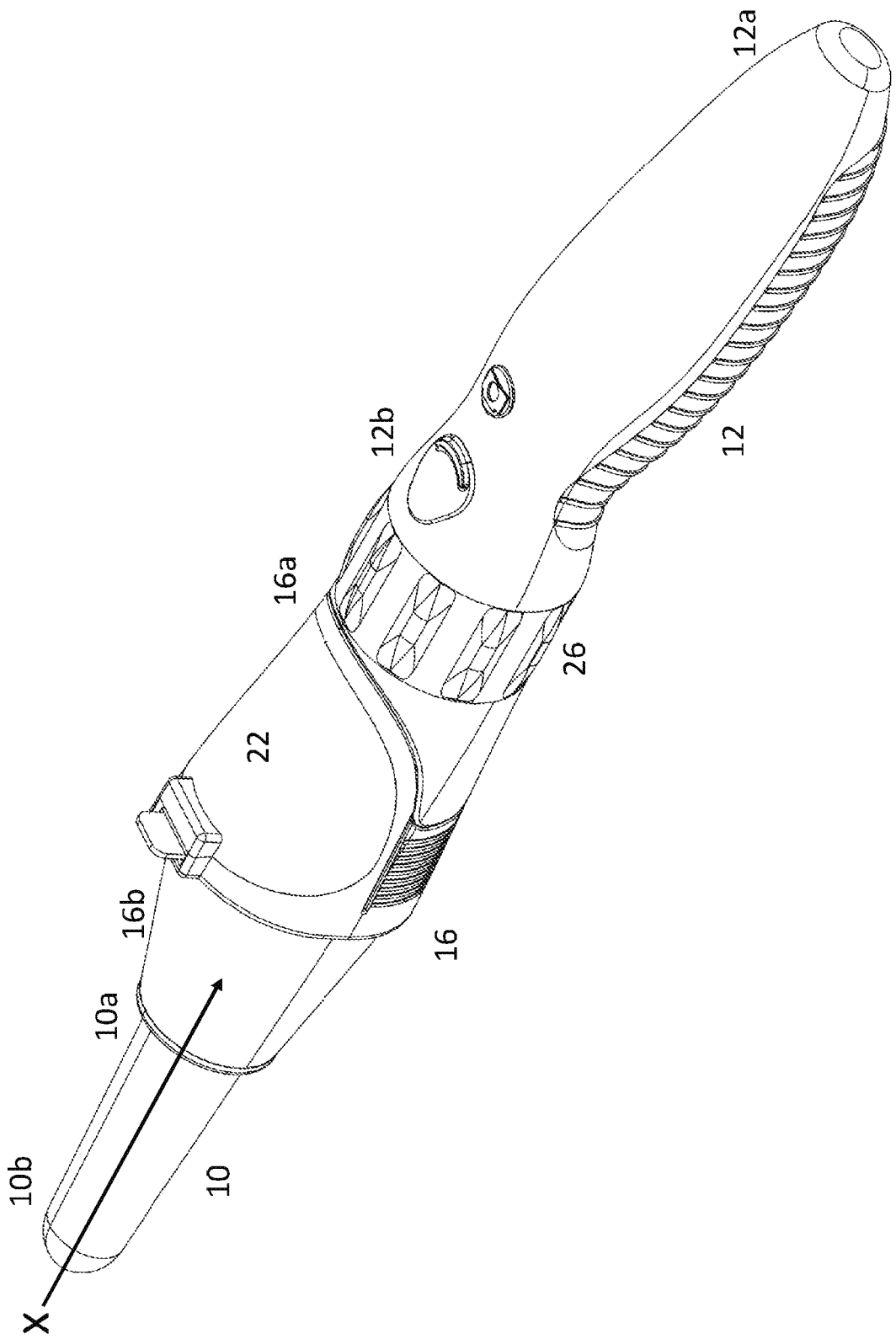
FIG. 1 is a perspective view of one embodiment of the scope.
Figure 2:
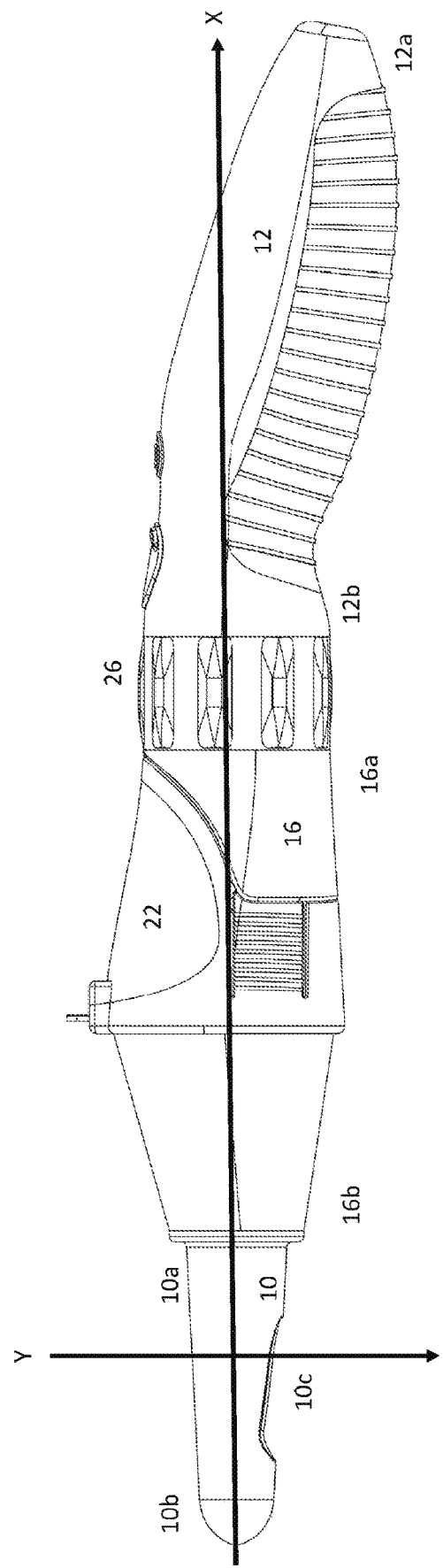
FIG. 2 is a side view of one embodiment of the scope.

As illustrated in FIGS. 1, 2 and 5, the scope comprises a tubular casing (10), wherein the tubular casing (10) comprises a proximal end (10*a*), a distal end (10*b*) and an internal volume (V1). As used herein, the term "proximal" refers to the component of the device that is nearest the user of the device, the physician (interchangeable with the term surgeon) or operator, and the term "distal" refers to the component of the device that is furthest away from the physician or operator.

Figure 3:
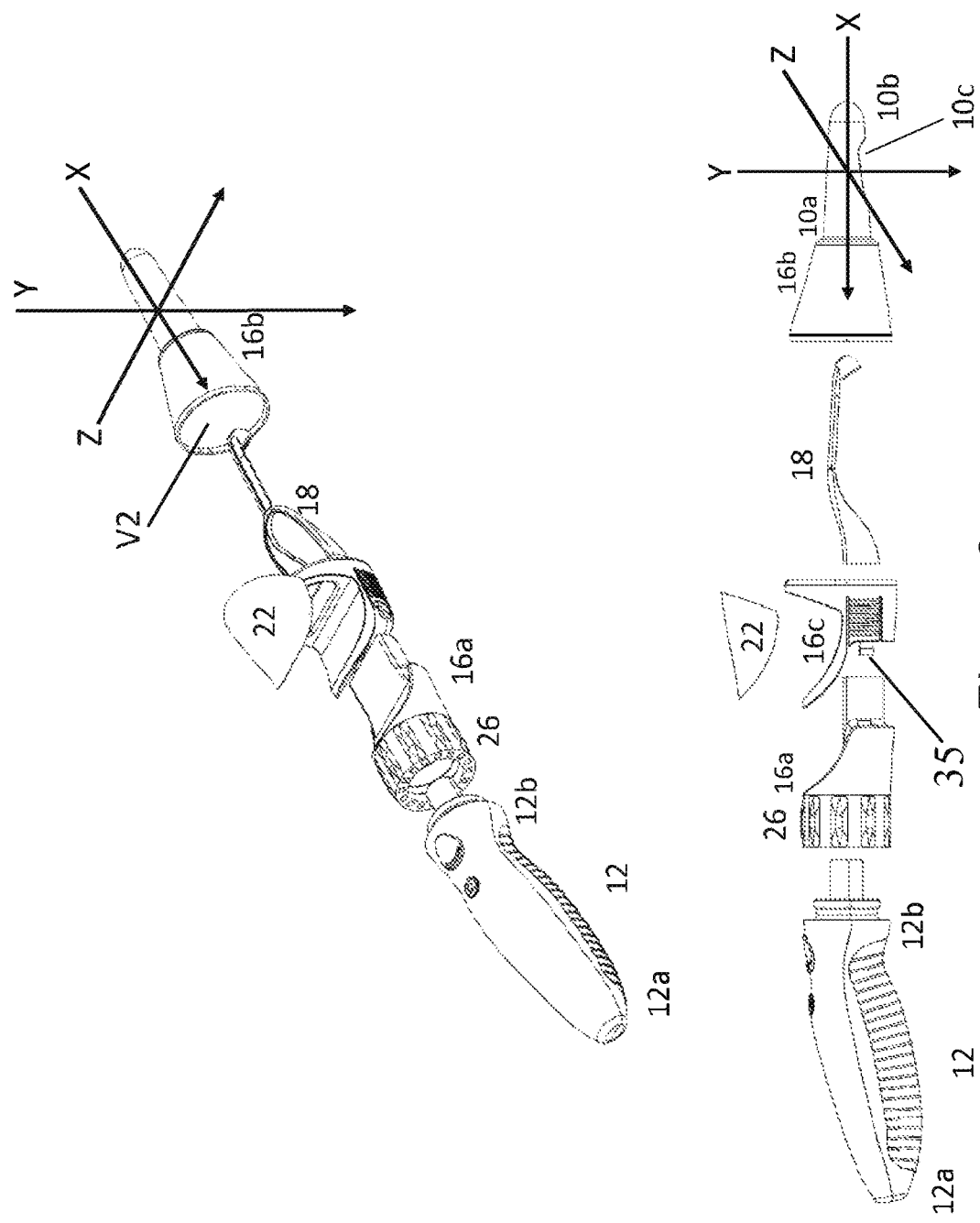
FIG. 3 is an exploded view showing the components of one embodiment of the scope.
Figure 4:
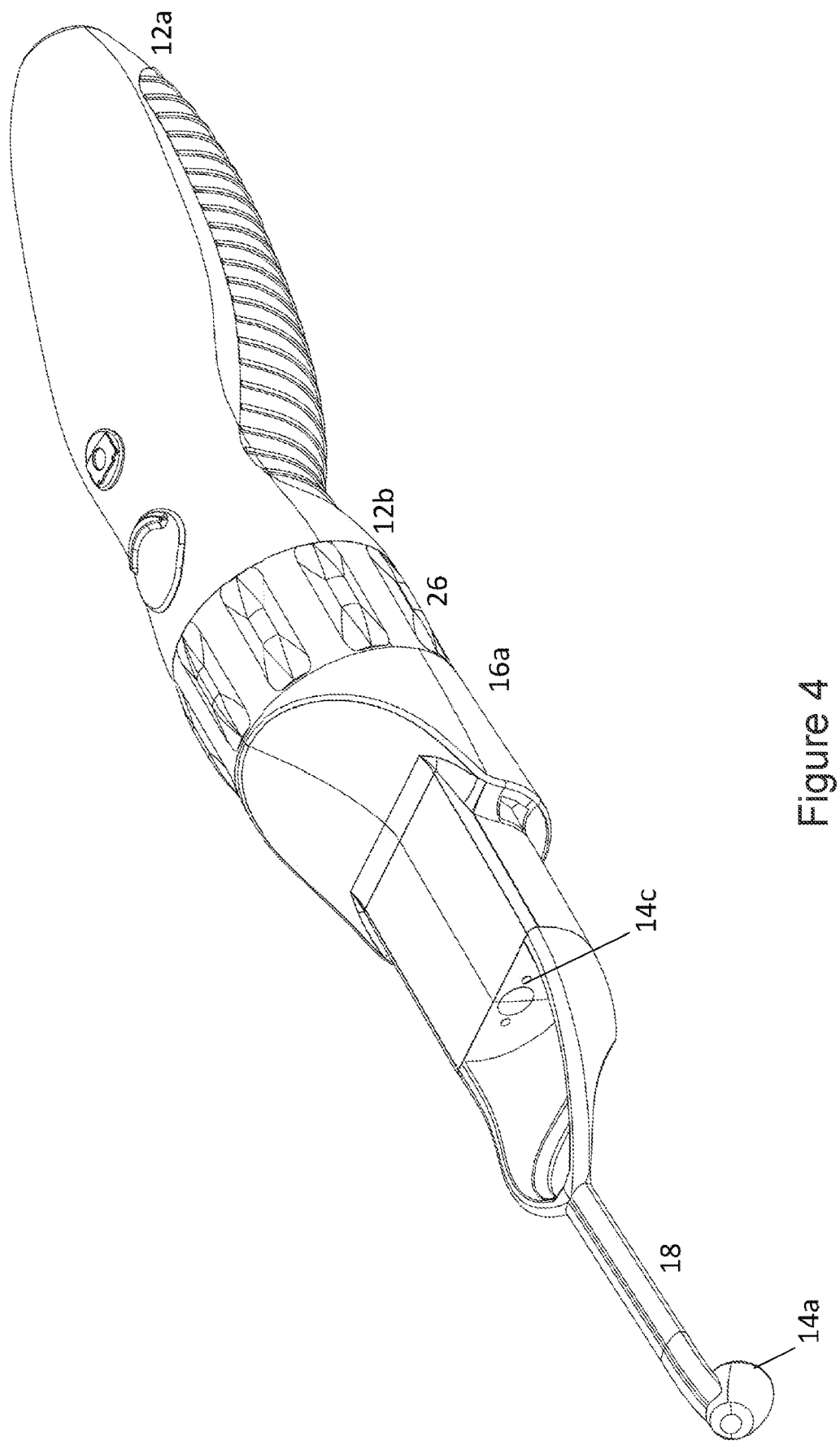
FIG. 4 is a perspective view of the handle and intermediate portion of one embodiment of the scope and shows one position for the rearward camera.

The tubular casing (10) has a longitudinal axis of extension (X) extending from the proximal end (10*a*) to the distal end (10*b*). The tubular casing (10) defines a hollow elongate body wherein the proximal end (10*a*) and the distal end (10*b*) are at opposite ends of the longitudinal axis of extension (X). The tubular casing (10) further has a vertical axis (Y) extending perpendicularly to the axis of extension (X), as show in FIG. 2. As illustrated in FIGS. 2 and 3, the tubular casing also comprises one or more openings (10*c*) along the length L of the longitudinal axis of extension (X).

In use, the tubular casing is inserted into the anus of the patient and serves to part the anal canal. It is inherent that the tubular casing (10) has both an inner surface and an outer surface. The outer surface of the tubular casing (10) is in contact with the anal cavity and/or rectal cavity when the scope is inserted into the anus. The inner surface of the tubular casing (10) defines the inner volume V1 of the tubular casing. The internal volume (V1) houses the one or more image capture devices of the present disclosure. The one or more openings (10*c*) expose a portion of to the anal or rectal anatomy to the internal volume (V1) which can be captured by the one or more image capture devices.

The tubular casing (10) can be either cylindrical or conical. The proximal end (10*a*) and the distal end (10*b*) of the tubular casing together form a cylindrical or conical hollow shape having a circular cross-section. In one embodiment, the width of the cross-section of the proximal end (10*a*) is substantially equal to the width of the cross-section of the distal end (10*b*) (i.e. the tubular casing (10) is cylindrical).

Preferably, as illustrated in FIG. 5, the cross-sectional profile of the tubular casing has a maximum width (W2) at the proximal end (10*a*) of the tubular casing and the width decreases (i.e. tapers) to a minimum width (W1) at the distal end (10*b*) of the tubular casing thereby aiding insertion of the scope into the anal canal. The width of the cross-section at the proximal end (10*a*) of the tubular casing (10) is therefore greater than the width of cross-section at the distal end (10*b*) of the tubular casing (10). In this embodiment, the tubular casing is tapered from proximal end (10*a*) to the distal end (10*b*). A conical or tapered tubular casing is preferred since the conical shape aids insertion of the scope into the anal canal.

In one embodiment, the cross-sectional profile of the tubular casing has a width (W1 or W2) of between 0.5 cm and 6 cm, optionally between 1 cm and 5 cm, further optionally between 2 cm and 4 cm. In one embodiment, the cross-sectional profile of the tubular casing has a width (W1) of between 0.5 cm and 6 cm, optionally between 1 cm and 5 cm, further optionally between 2 cm and 4 cm. In one embodiment, the cross-sectional profile of the tubular casing has a width (W2) of between 0.5 cm and 6 cm, optionally between 1 cm and 5 cm, further optionally between 2 cm and 4 cm.

The tubular casing (10) at the distal end (10*b*) may be open ended. Alternatively, in a preferred embodiment the tubular casing may be sealed or capped at the distal end. The cap may be dome shaped or bullet shaped to aid insertion of the tubular casing (10) into the anus.

Preferably, the tubular casing of the scope is sized and shaped to allow comfortable insertion into a patient's anus, without risking damage to the surrounding structures. As such the scope may have the dimensions of a conventional anoscope. In one embodiment, the tubular casing (10) has a length of 4 to 11 cm, optionally 7 to 10 cm. In one embodiment, the scope is a proctoscope. As such the scope may have the dimensions of a conventional proctoscope. In one embodiment, the tubular casing (10) has a length of 12 to 18 cm, optionally 13 to 14 cm. In one embodiment, the scope is a rectoscope. As such the scope may have the dimensions of a conventional rectoscope. In one embodiment, the tubular casing (10) has a length of 17 to 27 cm, optionally 18 to 26 cm. Other tubular casing lengths and widths are envisaged for use in smaller or larger patients or for use in paediatrics. In one embodiment, the scope is for use in humans. In one embodiment, the scope is for use in adults. In one embodiment, the scope is for use in children. In one embodiment, the tubular casing (10) is of sufficient length for insertion into the anus of the patient. In one embodiment, the tubular casing (10) is of sufficient length for insertion into the rectum of the patient.

The tubular casing comprises (10) one or more openings (10c) along the length L of the longitudinal axis of extension (X). In use, the rigid scope is inserted into a patient's anus and the opening exposes a targeted portion of the anal canal to the internal space of the tubular casing. The exposure of the mucosa or tissues of the anal or rectal anatomy enables a physician to investigate these areas or to perform surgical procedures on the exposed areas. Exposure of only a discrete area of the anatomy is highly desirable as enables the physician to perform surgical procedures on the area of interest only, whilst shielding the remainder of the tissue from surgical instruments. The one or more openings (10c) may be a gap, notch or a slot and are of a sufficient size to expose an anatomical site, for example a portion of the anal canal, of interest.

The one or more openings (10c) can be one or more apertures, i.e. one or more openings that go completely through the tubular casing. Use of one or more apertures is particularly advantageous as it allows a discrete portion of the anal passage to enter, via the aperture, the tubular casing. The portion of the anal canal that has entered the internal volume of the tubular casing can then be viewed from multiple angles, within the internal volume of the tubular casing (10) using the image capture devices of the present disclosure. Furthermore, the portion of the anal canal that has been isolated and situated within the internal volume of the tubular casing can be targeted with surgical tools that are passed through the device, thereby allowing seamless surgical intervention on the target area of the anal canal. Allowing a portion of the anal canal to enter the device, via the aperture, is surprisingly advantageous as it allows the operator of the device to visualise the dentate line and therefore establish the demarcation of somatically innervated tissue and visceral tissue. One particularly beneficial clinical use of the device is to surgically treat haemorrhoids. By using a device having a tubular casing comprising one or more apertures along the length L of the longitudinal axis of extension (X), the device can be targeted towards a haemorrhoid. Once located, the haemorrhoid can be guided and positioned into the tubular casing by locating the aperture directly above the haemorrhoid. Once the haemorrhoid is situated within the tubular casing it can be viewed and surgical intervention can be performed with greater ease than if the tissue was left outside of the tubular casing.

In one embodiment the edge of the aperture can be curved, providing a convex surface between the external surface and the internal surface of the tubular casing (10). The provision of a convex surface allows the entry of the anal passage into the internal volume of the tubular casing (10) without damaging the tissue.

In one embodiment, the aperture is elongate with a first (30) and second end (31), wherein the first end is located towards the distal end (10b) of the tubular casing. In some embodiments, the tubular casing may be sealed or capped at the distal end and the first end of the aperture is located towards the seal or cap (10). As shown in FIG. 16, the width of the first end (30) of the elongate aperture can be narrower than the second end (31) of the elongate aperture. In one embodiment, the aperture tapers from the second end to the first end of the aperture. In this embodiment, the shape of the aperture facilitates entry of the anal passage into the internal volume of the tubular casing (10).

In one embodiment, the one or more openings are approximately 0.5 cm to 5 cm in length, optionally 1 cm to 4 cm. The one or more openings (10c) are also of sufficient size to allow a medical instrument, for example snare & biopsy forceps, catheters, radio frequency ablation probes, suction haemorrhoidal banding equipment, needle and syringe to pass through the opening, from the internal volume (V1) of the tubular casing (10) to the anal canal or rectum. The scope may further comprise one or more covers for the one or more openings (10c) in the tubular casing (10). In one embodiment, the one or more covers for the one or more openings (10c) in the tubular casing (10) can be made of a transparent or partially transparent material, thereby acting as a window to the one or more openings (10c). In one embodiment, the one or more openings (10c) are a transparent window in the tubular casing (10). In one embodiment, the one or more covers for the one or more openings (10c) in the tubular casing (10) are retractable.

The tubular casing can be made of a rigid inflexible material such as medical grade plastic or biocompatible metal. In one embodiment, both the proximal end (10a) and the distal end (10b) of the tubular casing can be made of a rigid inflexible material. In one embodiment, either the proximal end (10a) or the distal end (10b) of the tubular casing can be made of a rigid inflexible material. In one embodiment, both the proximal end (10a) and the distal end (10b) of the tubular casing can be made of a transparent or partially transparent material. In one embodiment, either the proximal end (10a) or the distal end (10b) of the tubular casing can be made of a transparent or partially transparent material. Use of a rigid material as a tubular casing is advantageous as it permits use of the device as a proctoscope or anoscope, allowing for visualization of the anal passage with the image capture devices of the present disclosure, providing a unique perspective which cannot be seen with existing proctoscope and anoscope devices which lack image capture devices.

As shown in FIG. 1, the scope can further include an intermediate portion (16) having a proximal end (16a) and a distal end (16b) and wherein the distal end (16b) of the intermediate portion (16) is connected to the proximal end (10a) of the tubular casing (10) and the proximal end (16a) of the intermediate portion (12a) is connected to the handle (12). The intermediate portion may extend along the longitudinal axis of extension (x) of the tubular casing (10). Alternatively, the intermediate portion may be off-set to the longitudinal axis of extension (x) of the tubular casing (10). The intermediate portion does not enter the anus when the device is used.

The intermediate portion (16) may take any number of shapes. The intermediate portion (16) may form a cylindrical or conical shape having a circular cross-section. In one embodiment, the diameter of the cross-section of the proximal end (16a) is substantially equal to the cross-section of that of the distal end (16b) (i.e. the intermediate portion (16) is cylindrical). In one embodiment, the diameter of the cross-section of the distal end (16b) is less than that of the proximal end (16b) (i.e. the intermediate portion is conical). In this embodiment, the intermediate portion is tapered from distal end (16b) to the proximal end (16a). A flared or tapered shape prevents the intermediate portion (16) entering the anus when the scope is in use. Alternatively, or in addition, the intermediate region may also comprise an enlarged region or flange creating a stop. The stop prevents full insertion of the scope in the anal canal and ensures only the tubular casing (10) enters the anal canal.

Figure 13:
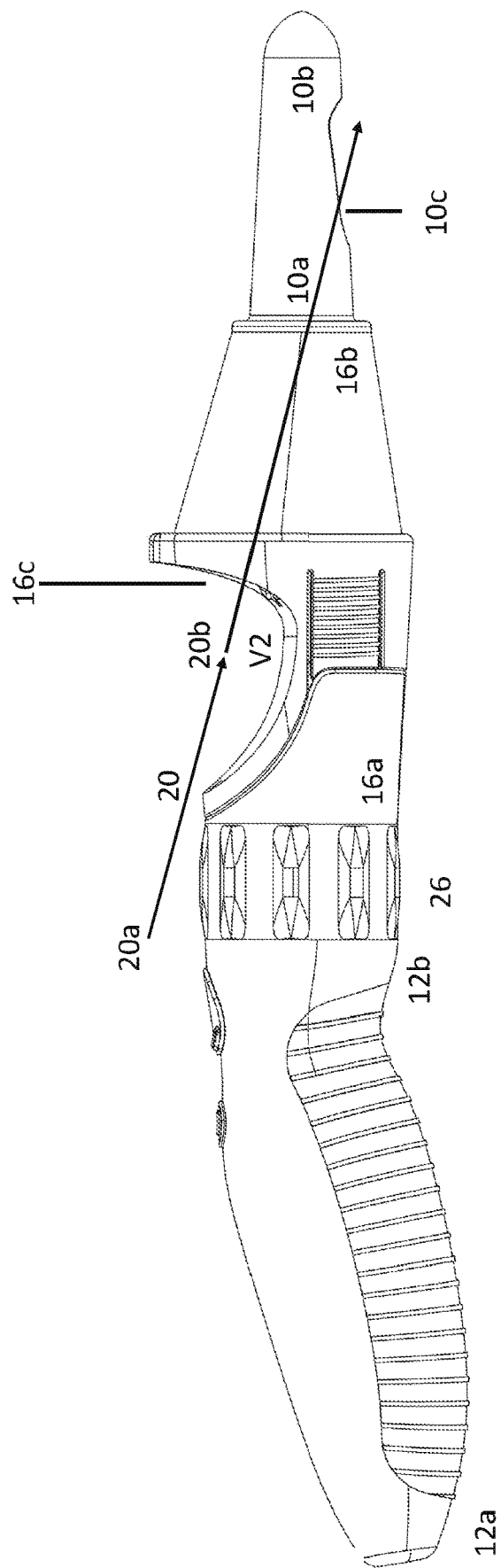
FIG. 13 provides a side view of the scope and shows the working channel in the scope.
Figure 14:
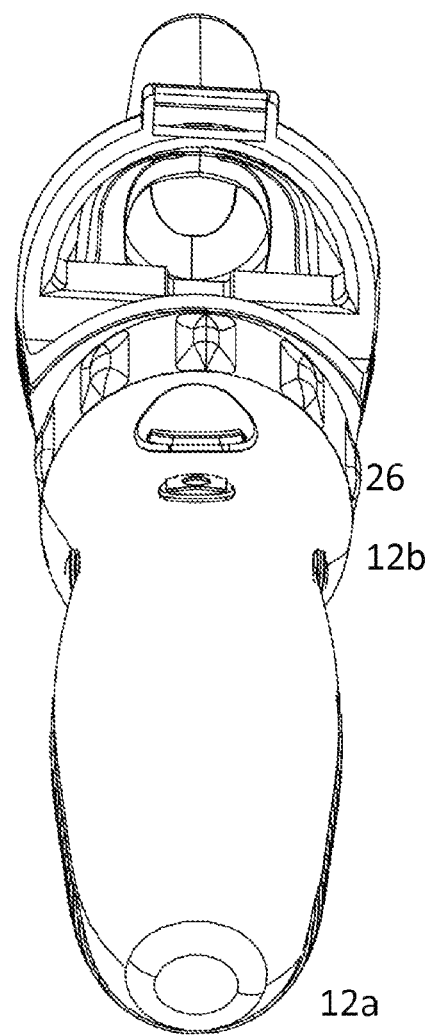
FIG. 14 provides a forward view of the scope.
Figure 15:
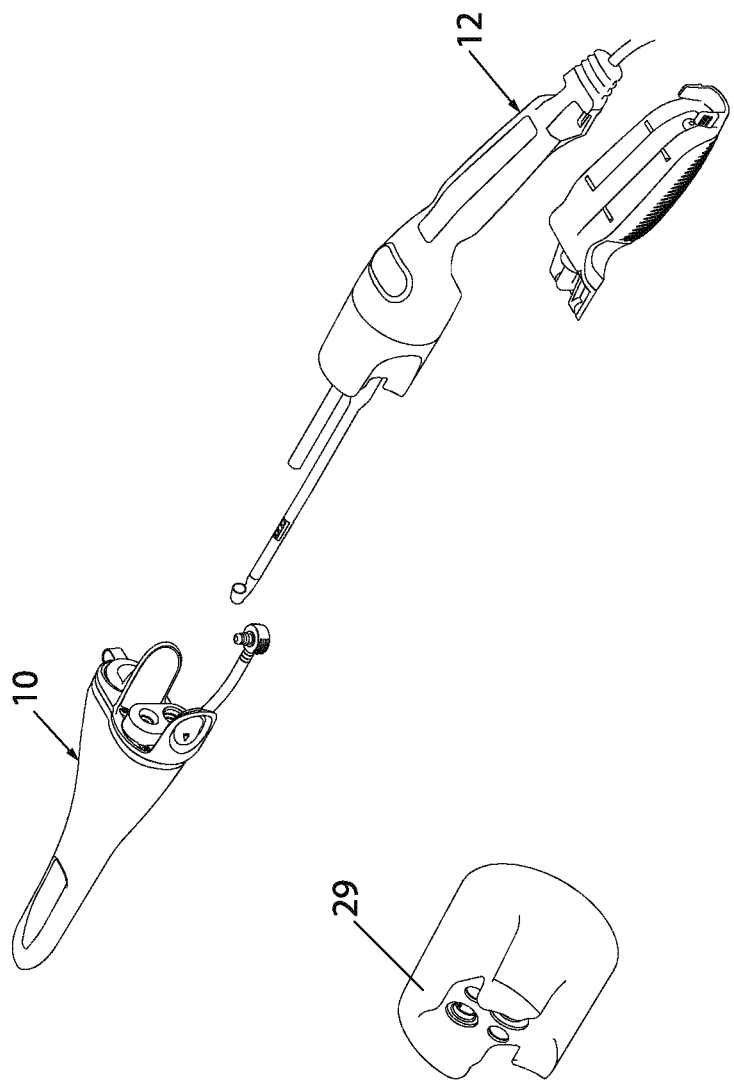
FIG. 15 provides a perspective view of the two projections that can be housed within the tubular casing.

The intermediate portion is preferably hollow. In this embodiment, the intermediate portion (16) has both an inner surface and an outer surface and comprises an internal volume (V2), as shown in FIGS. 3 and 13. The intermediate portion (16a) can further comprise a conduit (20) having a first external end (20a) and a second internal end (20b), as shown in FIG. 13, and extending from outside of said scope into the interior of the tubular casing (10) for insertion of surgical instruments into the internal volume (V2). The conduit provides a working channel, as shown by the arrows in FIG. 13, to allow the passage of surgical instruments through the device and allows the operator or physician to investigate or operate on the portion of tissue or mucosa exposed by the one or more openings (10c) in the tubular casing. In one embodiment, the conduit is offset with respect to the handle (see FIG. 16). The intermediate portion can have a proximal end (16a), a distal end (16b), a longitudinal axis of extension (x) and one or more openings (16c) along the length L of the longitudinal axis of extension (X). The one of more openings (16c) can be in the proximal end (16a) or the distal end (16b) of the intermediate portion and provide the entrance point into the internal volume (V2) of the device. The operator or physician can insert a surgical tool, for example snare & biopsy forceps, catheters, radio frequency ablation probes, suction haemorrhoidal banding equipment, needle and syringe, into the scope via the one of more openings (16c) in the intermediate portion (16) and manoeuvre the surgical tool through the internal space in the intermediate portion (V2) and the internal space in the tubular casing (V1) and then access the site of interest via the one of more openings (10c) in the tubular casing. Advantageously, the present present disclosure allows a surgical procedure to be performed at the same time, or shortly after, investigation of a site of interest.

The intermediate portion (16) can further comprises a cover (22) for covering the one or more openings (16c) in the intermediate portion (16). The cover (22) can either be in an open position wherein access to the internal space (V2) of the scope is permitted or in a shut position wherein the cover seals the internal space of the device. Advantageously, closing the cover (22) can seal the intermediate portion and provide a closed system. FIGS. 1 and 2 show the scope with a cover (22) in the closed position, sealing the one or more openings (16c) in the intermediate portion (16) shut. FIG. 3 shows the scope in an exploded view and shows the cover (22) and the one or more openings (16c) in the intermediate portion. A latch mechanism can be provided for releasably securing the cover to the intermediate portion (16) and allowing the cover to open and close. In one embodiment, the mechanism is a push-latch. Alternatively, the mechanism for opening and closing the cover (22) can be a twitch latch or a magnet. The latch mechanism can be located at either the proximal (16a) or the distal end (16b) of the intermediate portion. In a preferred embodiment, the latch mechanism sits flush with the outer surface of the intermediate portion.

The scope further comprises a handle (12) having a proximal end (12a) and a distal end (12b). The handle remains outside the body and is not inserted into the anus when the scope is in use. The handle can comprise a gripping means.

The tubular casing (10) can be removably connected to the intermediate portion (16) or the handle (12) of the device. This allows the tubular casing to be replaced between patients or cleaned before re-use. FIGS. 4, 6, 8, 9 and 10, show the scope with the tubular casing (10) removed and showing the components of the intermediate portion (16) and handle (12) only. In one embodiment, the tubular casing (10) can be disposable and therefore replaced between patients. In one embodiment, the intermediate portion can be removably connected to the handle (12) of the device. In one embodiment, the tubular casing (10) and the intermediate portion can be removably connected to the handle (12) of the device.

The scope further comprises one or more image capture devices (14) located towards the distal end (10b) of the tubular casing (10) and within the internal volume (V1) of the tubular casing (10) and wherein one or more image capture devices (14) is a rearward camera (14a) looking along an axis (b) extending between the longitudinal axis of extension (X) and the vertical axis (Y). As detailed in FIG. 3, the rearward camera (14a) is positioned in the internal volume (V1) of the tubular casing and the tubular casing (10) therefore provides a barrier between the camera and the anal anatomy. The field of vision of the rearward camera (14a) encompasses a view looking along an axis (z) extending from the internal volume (V1) of the tubular casing to the outside of said scope via the one or more openings (10c).

Figure 11:
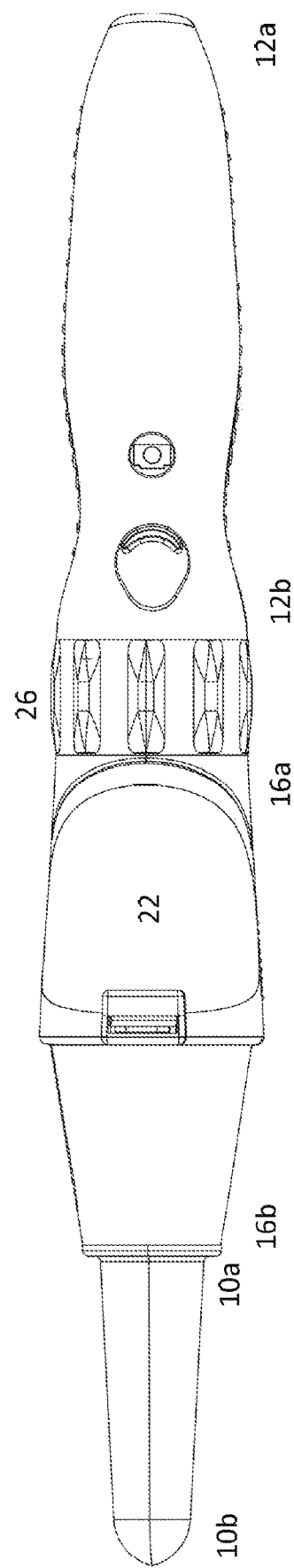
FIG. 11 is a top view of the one embodiment of the scope.
Figure 12:
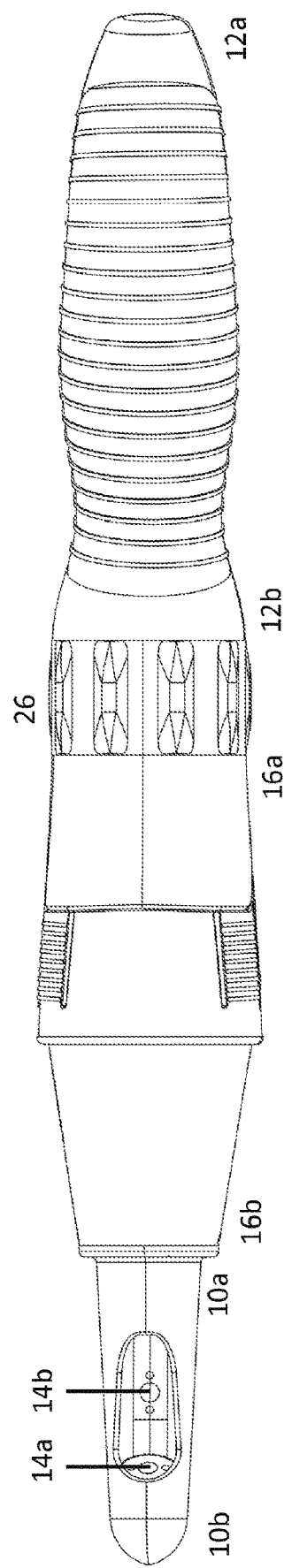
FIG. 12 provides a bottom view of the scope.

When in use, the distal end (10b) of the tubular casing is inserted furthest into the anal passage, and the proximal end (10a) is the end of the tubular casing that is situated at the entrance to the anus. The view looking down the device to the anal passage, from the proximal end (10a) to the distal end (10b) of the tubular casing, can be considered a "forward" direction. The rearward camera (14a) faces the opposite direction, so faces away from the distal end (10b) of the tubular casing and instead the lens of the rearward camera (14a) generally faces the proximal end (10a) of the tubular casing (i.e. looking internally from the anal passage towards the external portion of the device). The rearward camera advantageously provides a rearward view to the physician or operator, without the need for the physician or operator to be in close proximity to the device. As shown in FIGS. 3 and 11, the rearward camera (14a) is preferably positioned to capture an image through the one or more openings (10c) in the tubular casing. The rearward camera (14a) therefore also provides a viewpoint of the internal volume of the tubular casing (10). In this regard, the rearward camera (14a) looks along an axis (b) extending between the longitudinal axis of extension (X) and the vertical axis (Y). The axis may be an axis of extension (y) from the distal end (10b) to the proximal end (10a) of the tubular casing (10). As illustrated in FIG. 5, it will be appreciated that there are numerous axis (b) variations that extend between the longitudinal axis of extension (X) and the vertical axis (Y). An axis extending between the longitudinal axis of extension (X) and the vertical axis (Y) may extend from any point of the inner surface of the distal end (10b) of the tubular casing to any point of the inner surface of the proximal end (10a). In this way, the rearward camera (14a) generally points towards the proximal end (10a) of the tubular casing.

Preferably, the field of view of the rearward camera (14a) can encompass a view looking along an axis (b) extending from the internal volume (V1) of the tubular casing to the outside of said scope via the one or more openings (10c). Field of view is used to refer to the observable area in an image captured by the image capture device of the present disclosure. Field of view may be used interchangeably with the term viewing angle or angular field of view. Field of view as used herein can be understood to refer to either horizontal field of view (the observable area in a horizontal plane) or vertical field of view (the observable area in a vertical plane). Field of view can be quantified by a measurement of degrees in an angle. It is understood that the specific field of view will be determined by the specific image sensor and the specific length of the lens used in the one or more image capture devices of the present disclosure. It will be appreciated that various CMOS based cameras, image sensors and lenses are envisaged for use in the present disclosure and the image capture devices of the present disclosure may comprise a sensor and/or a lens that provides full high-definition (1080p) image capture. It is further appreciated that the scope may be provided with suitable power sources, such as batteries, cables and wires to provide power to the cameras. In addition, it is appreciated that the scope may be provided with suitable cables, leads and connection means to allow the transmission of images from the camera to an external viewing platform, such as an external display screen or computer. The scope may be provide with one or buttons, preferably located on the handle (12), that allow image capture.

It will further be appreciated that there are numerous possible axes (b) that are possible. In one embodiment, the field of view of the rearward camera (14a) encompasses at least a portion of the one or more openings. In one embodiment, the field of vision of the rearward camera (14a) encompasses the one or more openings. In one embodiment, the field of vision of the rearward camera (14a) encompasses a view looking along an axis (b) extending from the inner surface of the proximal end (10a) of the tubular casing to the outside of said scope via the one or more openings (10c). In one embodiment, the field of vision of the rearward camera (14a) encompasses a view looking along an axis (b) extending from the inner surface of the distal end (10b) of the tubular casing to the outside of said scope via the one or more openings (10c).

In one embodiment, the axis (b) for the rearward camera (14a) is the longitudinal axis of extension (x) from the distal end (10b) to the proximal end (10a) of the tubular casing (10), i.e. the axis running lengthwise through the centre of the tubular casing (10). In one embodiment, the rearward camera (14a) looks along an axis (b) from the distal end (10b) to the proximal end (10a) of the tubular casing (10); and wherein the field of view of the camera encompasses a view looking along an axis (b) extending from the internal volume (V1) of the tubular casing to the outside of said scope via the one or more openings (10c).

It will be appreciated that the rearward camera can also look along an axis (c) extending between the longitudinal axis of extension (X) and the lateral axis (Z). The lateral axis (Z) extends perpendicularly to the longitudinal axis of extension (X) and perpendicular to the vertical axis (Y). In some embodiments, the rearward camera looks along an axis (c) extending between the longitudinal axis of extension (X) and the lateral axis (Z), wherein the axis is within 75 degrees of the longitudinal axis of extension (X). In some embodiments, the axis is within 60 degrees, 45 degrees, 30 degrees or 15 degrees.

In some embodiments, the rearward camera (14a) can provide a view of the anorectal junction and dentate line. This is a particularly unique viewpoint that cannot be viewed with conventional anoscope devices.

It will be appreciated that there are numerous different positions at which the rearward camera (14a) can be located within the tubular casing (10) to provide the specified view. In one embodiment, the rearward camera (14a) is mounted to the inner surface of the distal end (10b) of the tubular casing (10). In one embodiment, the rearward camera (14a) is mounted to a support member attached to the inner surface of the distal end (10b) of the tubular casing (10). In one embodiment, the scope comprises a projection having a first end mounted on the inner surface of the proximal end (10a) of the tubular casing (10) and extending towards the distal end (10b) of the tubular casing (10). In one embodiment, as illustrated in FIG. 3, the scope comprises a projection (18) having a first end (18a) mounted on the distal end of the intermediate portion (16b) and extending along axis X towards the distal end (10b) within the tubular casing (10) and wherein rearward camera (14a) is mounted on the projection (18). The projection (18) can be bifurcated, as illustrated in FIG. 3.

The rearward camera (14a) can be fixed in position. There is therefore no need to manoeuvre the device to capture the viewpoint provided by the rearward camera (14a). In one embodiment, the camera is fixedly attached to the inner surface of the tubular casing. In one embodiment, the camera is fixedly attached to a support member of projection as described herein.

Conventional proctoscope devices are limited in the views they provide and are frequently limited to a single view and/or a very narrow field of vision, meaning that they physician may miss a significant clinical feature or area of clinical abnormality. The present disclosure allows multiple simultaneous images can be provided by the one or more image capture devices of the scope. This allows visualization of a site of interest in the anal canal or rectum in multiple dimensions using a simple, portable device. Capturing multiple complementary images in different planes of view using the scope of the present disclosure can be advantageous for the physician as it allows to closely observe the anatomy of the site of interest and can result in the identification of features or clinical abnormalities that may otherwise be missed. It also enables faster examination of the anus, therefore reducing the time that the device is inserted into the anus. This reduces both patient discomfort, as well as enabling the physician to perform more investigations and surgical procedures in a shorter space of time.

Figure 7:
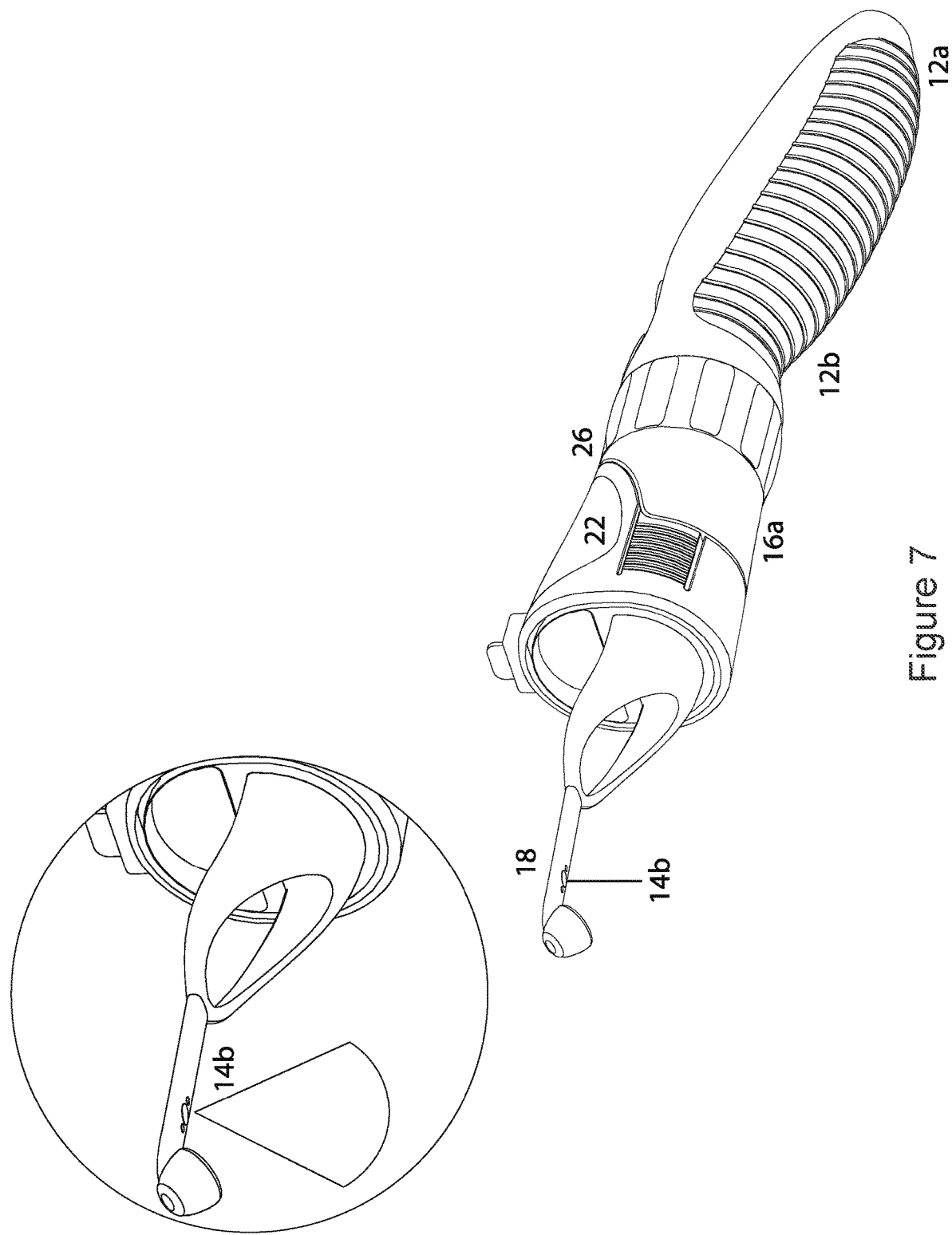
FIG. 7 is a perspective view of the handle and intermediate portion of one embodiment of the scope and shows one position for the sideward camera. The field of view of the sideward camera is shown in the circle.

As shown in FIG. 7, the scope can optionally further comprise a sideward camera (14b) located within the internal volume (V1) of the tubular casing (10) and wherein the sideward camera is looking along the vertical axis (y) and through the opening (10c) in the tubular casing (10). The lens of the sideward camera (14b) faces the one or more openings (10c).

Figure 8:
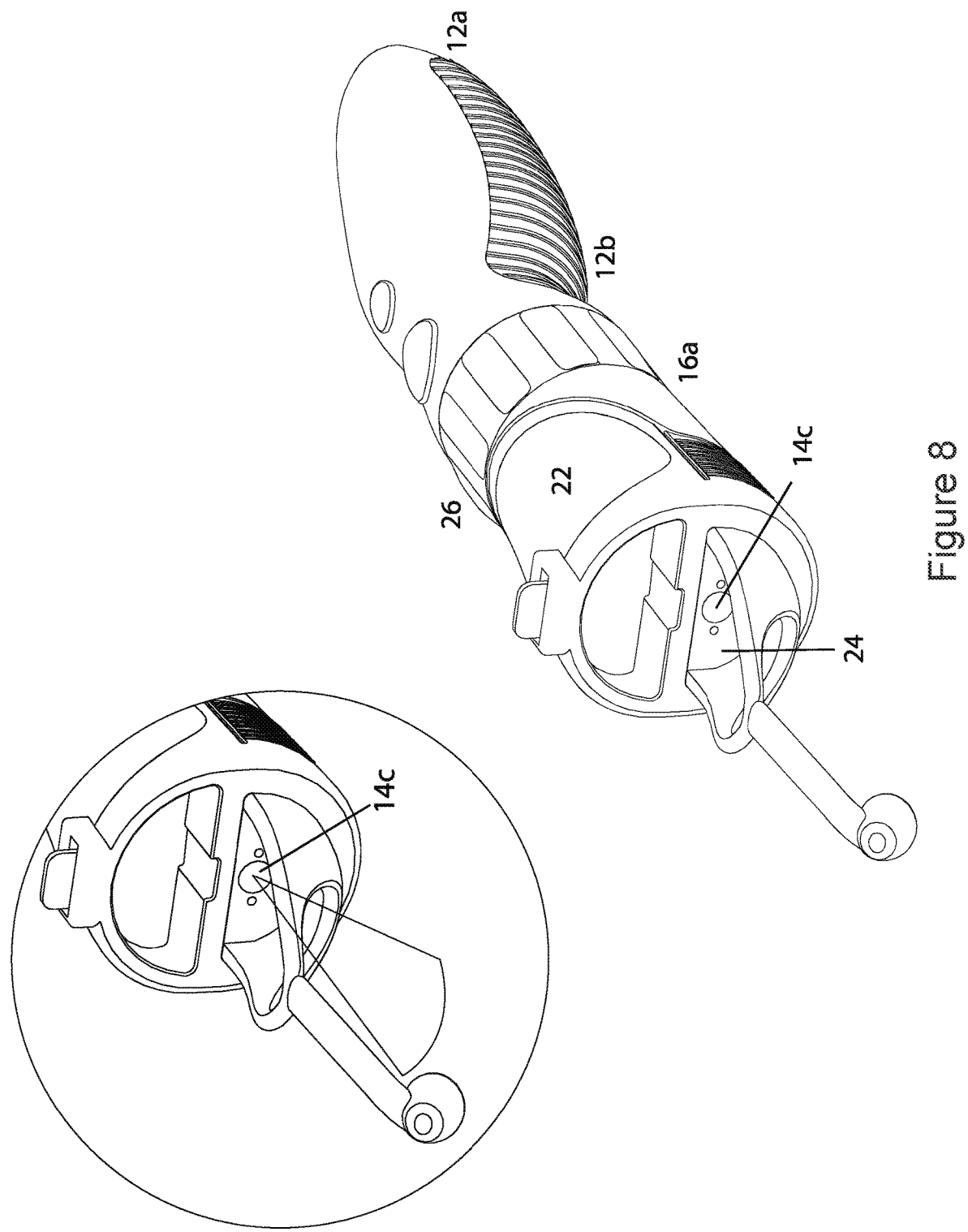
FIG. 8 is a perspective view of the handle and intermediate portion of one embodiment of the scope and shows one position for the forward camera. The field of view of the forward camera is shown in the circle.
Figure 9:
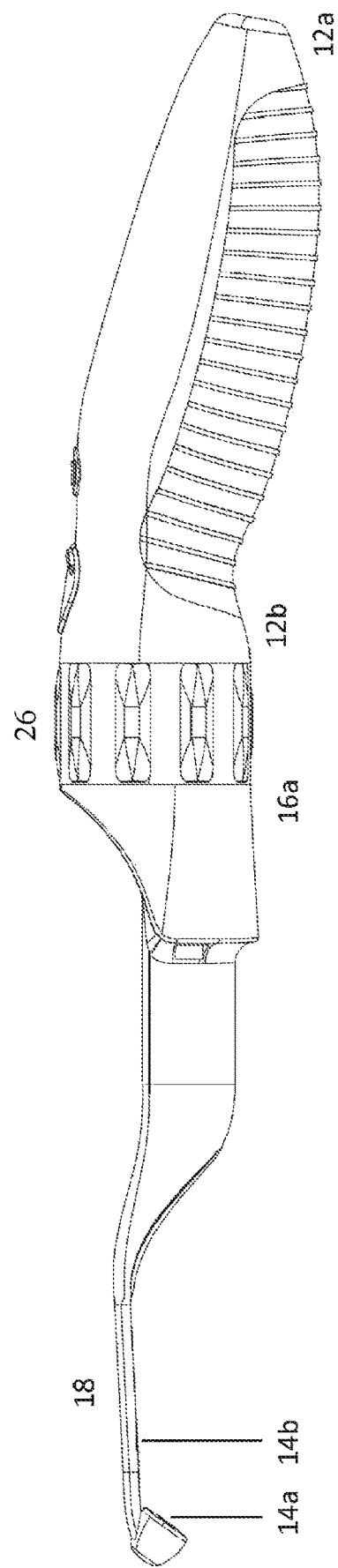
FIG. 9 is a side view of the handle and intermediate portion of one embodiment of the scope.
Figure 10:
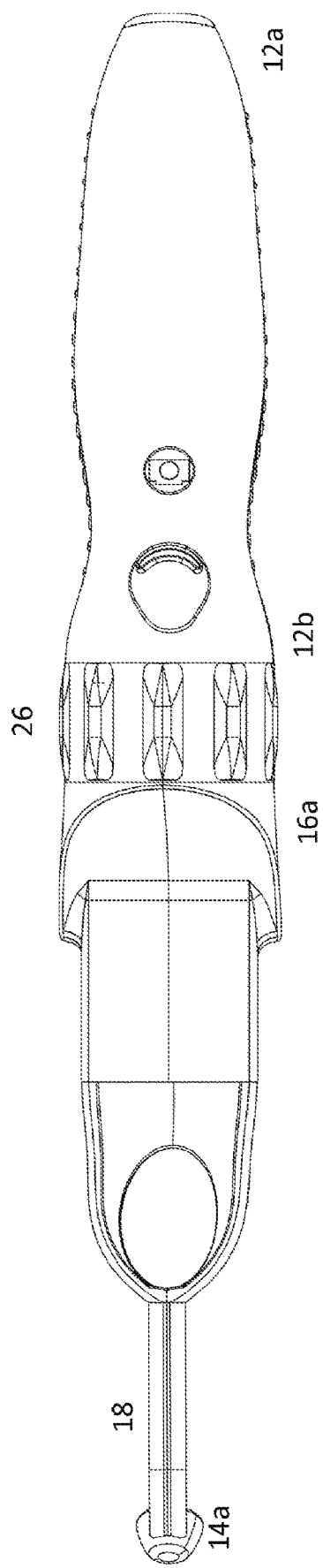
FIG. 10 is a top view of the handle and intermediate portion of one embodiment of the scope.

As shown in FIG. 8, the scope can optionally further comprise a forward camera (14c) looking along the longitudinal axis of extension (x) from the proximal end (10a) to the distal end (10b) of the tubular casing (10). The forward camera (14c) provides the view from the proximal end (10a)

to the distal end (10b) of the tubular casing, so looking forwards from the intermediate portion or handle into the anal passage. The lens of the forward camera (14c) faces the distal end (10b) of the tubular casing and captures an image in the direction of the distal end (10b) of the tubular casing. In use, the forward camera can be used to capture views of the perineum and the areas surrounding the anus. This can be done by the physician using the scope prior to insertion into the anus by using the scope to examine the area external to the anus. As the tubular casing (10) is inserted into the anus, the forward camera will look forward through the device and can therefore also capture images of the anal camera and anal verge.

The forward camera can be located in the internal volume (V1) of the tubular casing. Alternatively, the forward camera can be located in the internal volume (V2) in the intermediate portion. In one embodiment, as shown in FIG. 8, the intermediate portion (16) further comprises an outer surface, an inner surface and a support member (24) attached to the inner surface and wherein the forward camera (14c) is mounted on the support member (24). The support member may extend across the full cross-section of the intermediate portion (16).

Figure 6:
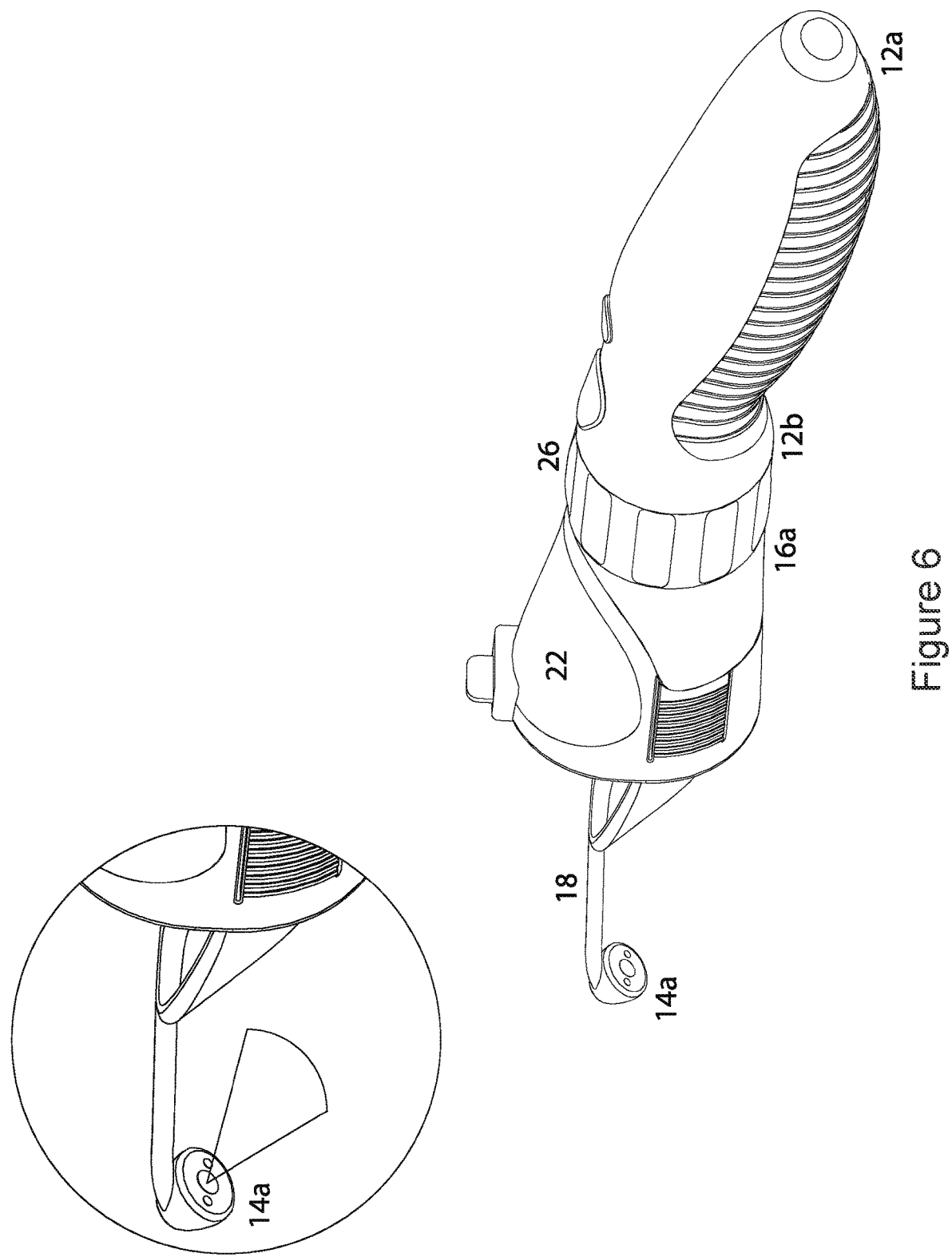
FIG. 6 is a perspective view of the handle and intermediate portion of one embodiment of the scope and shows one position for the rearward camera. The field of view of the rearward camera is shown in the circle.

In some embodiments, the one or more image capture devices of the scope comprise a field of view of 45 degrees or less. A field of view of the rearward camera (14a) of approximately 45 degrees is shown in FIG. 6. A field of view of the sideward camera (14b) of approximately 45 degrees is shown in FIG. 7. In some embodiments, the one or more image capture devices of the scope comprise a field of view of 45 degrees or more. In some embodiments, the one or more image capture devices of the scope comprise a field of view of 90, 120, 150 or 180 degrees or less. In some embodiments, the one or more image capture devices of the scope comprise a field of view of 90, 120, 150 or 180 degrees or more. In some embodiments, the one or more image capture devices of the scope has a field of view between 45 degrees and 90 degrees, between 45 degrees and 120 degrees, between 45 degrees and 150 degrees or between 45 degrees and 180 degrees.

The lens of the rearward camera (14a) of the scope and the lens of the forward camera (14c) of the scope may point in directions essentially towards each other along the longitudinal axis of extension (x).

In some embodiments, the rearward camera (14a) and the sideward camera (14b) are pointing in directions essentially perpendicular to one another. Correspondingly, the rearward (14a) and the sideward camera (14b) will have perpendicular fields of view. In some embodiments, the rearward camera (14a) and the sideward camera (14b) are pointing approximately 90 degrees relative to each other- the rearward camera (14a) pointing in the direction of the proximal end (10a) of the tubular casing (10) and the sideward camera (14b) pointing in the direction of the one or more openings (10c) in the tubular casing.

In some embodiments, the rearward camera (14a) and the sideward camera (14b) are pointing approximately 45 degrees relative to each other- the rearward camera (14a) pointing generally in the direction of the proximal end (10a) of the tubular casing (10) and also pointing in the direction of the one or more openings (10c) in the tubular casing, and the sideward camera (14b) pointing in the direction of the one or more openings (10c) in the tubular casing.

In some embodiments, the forward camera (14c) and the sideward camera (14b) are pointing in directions essentially perpendicular to one another. Correspondingly, the forward camera (14c) and the sideward camera (14b) will have perpendicular fields of view. In some embodiments, the forward camera (14c) and the sideward camera (14b) are pointing approximately 90 degrees relative to each other- the forward camera (14c) pointing in the direction of the distal end (10b) of the tubular casing (10) and the sideward camera (14b) pointing in the direction of the one or more openings (10c) in the tubular casing. It is to be understood that the angles of the camera relative to each other can vary, for example the two cameras may be pointing approximately 60, 70, 80, 90, 100, 110 or 120 degrees relative to each other.

In some embodiments, rearward camera (14a) and the sideward camera (14b) are pointing in directions essentially perpendicular to one another, and the forward camera (14c) and the sideward camera (14b) are pointing in directions essentially perpendicular to one another. In this embodiment, the forward and the rearward camera (14a) may point in directions essentially towards each other along the longitudinal axis of extension (x).

In some embodiments, the fields of view of the one or more image capture devices are overlapping or partially overlapping. Advantageously, the fields of view of the one or more, two or more, or three or more cameras overlap or partially overlap such each camera views the same object of interest through the one or more openings (10c) in the tubular casing (10). In this instance, the object of interest is the same however the cameras advantageously provide different viewpoints of the object to aid the physician in their investigation and/or surgical intervention of the object or abnormality. In one embodiment, the fields of view of the rearward camera (14a) and the sideward camera (14b) are at least partially overlapping. In one embodiment, the fields of view of the rearward camera (14a) and the sideward camera (14b) are overlapping. In one embodiment, the fields of view of the rearward camera, (14a) the forward camera (14c) and the sideward camera (14b) are at least partially overlapping. In one embodiment, the fields of view of the rearward camera (14a), the forward camera (14c) and the sideward camera (14b) are overlapping. In a preferred embodiment, the one or more openings in the tubular casing (10) are one or more apertures and the image capture devices of the present disclosure provide overlapping viewpoints of the internal volume of the tubular casing, thereby permitting multiple viewpoints of the discrete portion of the anal canal that has entered the internal space of the tubular casing, via the one or more apertures.

In one embodiment, the scope comprises the rearward camera (14a), the sideward camera (14b) and the forward camera to provide images in three planes.

Conventional proctoscopes utilise an obturator to aid entry of the device into the anal canal. The obturator is removably positioned within the hollow tube of a conventional proctoscope and the head of the obturator extends beyond the end of the proctoscope tube. In use, both the proctoscope and the obturator are inserted into the anus and the obturator head aids insertion by dilating the anal canal. The obturator is a removable component of a conventional proctoscope and is removed from the proctoscope after insertion into the anus, thereby allowing the physician to view or access the anal cavity. As the obturator is in contact with the tissue of the anal cavity, removal of the obturator can result in bodily fluids and faeces being pulled through the hollow tube of a conventional proctoscope. This can be unpleasant for the operator, as well as detrimental to the viewing of the internal structures of the anal cavity since the faeces or bodily fluids may adhere to the internal surface of the proctoscope and obscure the physician's viewpoint.

The present disclosure also provides device that do necessarily need to utilize a removeable obturator. The tubular casing (10) that functions to insert the image capture devices into the anal cavity remains present during use of the claimed scope. This advantageously means that the components of the claimed scope are not contaminated or obscured by bodily fluids, faeces or other substances during use of the scope. In one embodiment, the device is a single unit. In one embodiment, the scope does not comprise an obturator.

The intermediate portion (16) of the scope is optionally rotatably mounted on the handle (12) for rotation about said longitudinal axis X. A shown in FIG. 3, a dial (26) may be provided on the handle or the intermediate portion to allow rotation of intermediate portion (16) and the tubular casing (10) relative to the handle. The intermediate portion (16) or handle (12) may comprise a spindle or spigot about which the tubular casing (10) can be rotated. By rotating the tubular casing (10) the sideward camera (14b) can capture images circumferentially in the anal canal or rectum, through the one more openings (10c) in the device. The dial (26) can be turned by hand allowing the physician to carefully control the view point of the one or more image capture devices. Alternatively, the dial may be automated or rotated electronically or via firmware control.

The scope may further comprise light sources for projection light into the interior of the tubular casing (10). The light source may be any light source known the skilled person, including light emitting diode (LED) or ring lights. The one or more light sources can be encased within the tubular casing (10) and therefore located in the internal volume (V1) of the tubular casing. The light sources may be placed adjacent to the one or more image capture devices of the present disclosures or may encircle the one or more image capture devices of the present disclosures to provide light in the field of view of the camera.

The scope may further comprise a pressurising mechanism (28) for pressurising the interior of the tubular casing (10). In one embodiment, the pressuring mechanism (28) is a gas delivery mechanism. In one embodiment, the pressurising mechanism is a bellows. The pressurising means may also be an bulb pump, electric pump, pressurised air cartridge, canister or the like. Advantageously, the scope provides a closed system for insufflating air into the anus of a patient. Insufflation of air expands the tissue of interest thereby allowing it to be better visualized. Insufflation of air also reduces or eliminates any tissue folds in the anal canal or rectum which may reveal abnormalities or sites of interest that were previously hidden within the folds. The pressurising mechanism can be self-contained within the handle meaning there is no requirement for an external air supply. Preferably the pressuring mechanism for supplying air is partially or fully enclosed within the handle. The handle can further be provide with an actuating means to operate the pressurising mechanism and control the supply of air to the tubular casing (10).

In one aspect, a tubular casing (10) having a longitudinal axis of extension (X), a proximal end (10a), a distal end (10b), an internal volume (V1) and one or more openings (10c) along the length L of the longitudinal axis of extension (X) for a scope as defined herein is provided.

In one aspect, a scope for insertion into the anus is provided, wherein said scope comprises:
(a) a handle (12) having a proximal end (12a) and a distal end (12b) and a longitudinal axis of extension (X) extending from the proximal end (12a) to the distal end (12b); and (b) a projection (18) having a first end (18a) mounted on the distal end of the handle (12b) and projecting in the opposite direction to the proximal end of the handle (12a) and wherein a rearward camera is mounted on the projection and wherein the rearward camera looks along the longitudinal axis of extension (x) towards the proximal end of the handle (12a).

In further aspect the present disclosure relates to a scope for use in the sampling of the anus. In further aspect the present disclosure relates to a scope for use in the sampling of the rectum.

In further aspect the present disclosure relates to a method of treatment comprising inserting a scope into the anus and sampling, performing biopsy, removing, cauterizing or otherwise treating the anal canal.

In further aspect the present disclosure relates to a method of anorectal diagnosis comprising inserting the rigid scope into the anus, viewing, performing biopsy or otherwise examining the anus, and comparing the results with images or biopsies of known normal anus to diagnose disease.

In a further aspect, there is provided a method of diagnosis and treatment, optionally to the anorectal region, comprising
a) inserting a scope as described herein into the anus, viewing, performing biopsy or otherwise examining the anus, and comparing the results with images or biopsies of known normal anus to diagnose disease; and
b) treating the anus according to the disease diagnosis in a).

What is claimed is:

1. A scope comprising:
a tubular casing, a proximal end, a distal end, an internal volume, a longitudinal axis of extension extending from the distal end to the proximal end, a vertical axis extending perpendicularly to the longitudinal axis of extension and one or more apertures along a length L of the longitudinal axis of extension;
a handle having a proximal end and a distal end; and
image capture devices each located within the internal volume of the tubular casing, wherein the image capture devices comprise a rearward camera with a field of view through the one or more apertures in the tubular casing in a direction between the longitudinal axis of extension and the vertical axis, a sideward camera with a field of view through the one or more apertures in the tubular casing in a direction of the vertical axis, and a forward camera with a field of view through the one or more apertures in the tubular casing in a direction of the longitudinal axis of extension from the proximal end to the distal end of the tubular casing.

2. The scope of claim 1, further comprising an intermediate portion having a proximal end and a distal end and wherein the distal end of the intermediate portion is connected to the proximal end of the tubular casing casing, and the proximal end of the intermediate portion is connected to the handle.

3. The scope of claim 2, further comprising a projection having a first end mounted on the distal end of the intermediate portion and extending along the longitudinal axis of extension towards a distal end within the tubular casing and wherein the rearward camera is mounted on the projection.

4. The scope of claim 2, further comprising a projection having a first end mounted on the distal end of the intermediate portion and extending along the longitudinal axis of extension towards a distal end within the tubular casing and wherein the sideward camera is mounted on the projection.

5. The scope of claim 2, wherein the intermediate portion is further comprised of an outer surface, an inner surface and a support member attached to the inner surface, and wherein the forward camera is mounted on the support member.

6. The scope of claim 2, wherein the intermediate portion further comprises a conduit having a first external end and a second internal end and extending from outside of said scope into an interior of the tubular casing for insertion of surgical instruments into the internal volume.

7. The scope of claim 6, wherein the first external end is within the intermediate portion.

8. The scope of claim 6, wherein the intermediate portion further comprises a cover for covering the first external end of the conduit.

9. The scope of claim 8, further comprising a latch for releasably securing the cover to the intermediate portion.

10. The scope of claim 9, further comprising a latch release for releasing the latch and being positioned on the handle.

11. The scope of claim 1, wherein one or more of the one or more apertures is elongate with a first end and a second end and having a taper from the second end to the first end, wherein the first end is located towards the distal end of the tubular casing.

12. The scope of claim 1, wherein the tubular casing is rigid.

13. The scope of claim 1, further comprising a pressurising mechanism for pressurising an interior of the tubular casing.

14. The scope of claim 13, wherein the pressurising mechanism is contained within the handle and comprises bellows.

15. The scope of claim 1, wherein a cross-sectional profile of the tubular casing has a maximum diameter at the proximal end of the tubular casing and tapers to a minimum diameter at the distal end of the tubular casing.

16. The scope of claim 1, further comprising one or more covers for the one or more apertures in the tubular casing.

17. The scope of claim 1, further comprising a light source for projecting light into an interior of the tubular casing.

18. A scope comprising:
a handle having a proximal end and a distal end;
a longitudinal axis of extension extending from the proximal end to the distal end;
a vertical axis extending perpendicularly to the longitudinal axis of extension;
a tubular casing having an internal volume and one or more apertures along a length of the longitudinal axis of extension;
a projection having a first end mounted on the distal end of the handle and projecting in a direction opposite to the proximal end of the handle; and
image capture devices each located within the internal volume of the tubular casing, wherein the image capture devices comprise:
a rearward camera mounted on the projection with a field of view through the one or more apertures in the tubular casing in a direction between the longitudinal axis of extension and the vertical axis;
a sideward camera with a field of view through the one or more apertures in the tubular casing in a direction of the vertical axis; and
a forward camera with a field of view through the one or more apertures in the tubular casing in a direction of the longitudinal axis of extension from the proximal end to the distal end.

19. A method of treatment, comprising:
inserting a scope into an anus, the scope comprising:
a tubular casing, a proximal end, a distal end, an internal volume, a longitudinal axis of extension extending from the distal end to the proximal end, a vertical axis extending perpendicularly to the longitudinal axis of extension and one or more apertures along a length L of the longitudinal axis of extension;
a handle having a proximal end and a distal end; and
three image capture devices each located within the internal volume of the tubular casing, wherein the three image capture devices are a rearward camera with a field of view through the one or more apertures in the tubular casing in a direction between the longitudinal axis of extension and the vertical axis, a sideward camera with a field of view through the one or more apertures in the tubular casing in a direction of the vertical axis, and a forward camera with a field of view through the one or more apertures in the tubular casing in a direction of the longitudinal axis of extension from the proximal end to the distal end of the tubular casing;
conducting an examination of the anus using the scope; and
comparing results obtaining during the examination with information from a normal anus and diagnosing disease based on the comparison.

20. The method of claim 19, wherein examining the anus can include at least one of sampling, biopsying, surgically treating, and cauterizing the anus.

* * * * *